United States Patent
Chang et al.

(10) Patent No.: US 7,332,350 B2
(45) Date of Patent: Feb. 19, 2008

(54) DIAGNOSTIC DEVICE FOR DISTINGUISHING BETWEEN NORMAL AND ECTOPIC PREGNANCY AND METHOD FOR PREPARING THE SAME

(75) Inventors: Jin-Dong Chang, Yangcheon-gu (KR); Jung-Hak Cha, Gunpo-si (KR); Jung-Hyun Nam, Uiwang-si (KR)

(73) Assignee: Humasis Co., Ltd., Gyeonggi-do (KR)

( * ) Notice: Subject to any disclaimer, the term of this patent is extended or adjusted under 35 U.S.C. 154(b) by 532 days.

(21) Appl. No.: 10/364,715

(22) Filed: Feb. 10, 2003

(65) Prior Publication Data

US 2003/0153093 A1 Aug. 14, 2003

Related U.S. Application Data

(63) Continuation of application No. PCT/KR01/01365, filed on Aug. 10, 2001.

(30) Foreign Application Priority Data

Aug. 12, 2000 (KR) ................ 2000-46755

(51) Int. Cl.
*G01N 33/543* (2006.01)
(52) U.S. Cl. .............. 436/510; 436/518; 436/514; 436/548; 436/818; 435/7.1; 435/7.94
(58) Field of Classification Search ............. 436/518, 436/514, 510, 548, 818; 435/7.1, 7.94
See application file for complete search history.

(56) References Cited

U.S. PATENT DOCUMENTS 4,016,250 A    4/1977  Saxena ................. 424/1
5,185,270 A    2/1993  Senyei et al. ............... 436/510
5,236,846 A    8/1993  Senyei et al. ................. 436/65
5,786,220 A    7/1998  Pronovost et al. .......... 436/518

FOREIGN PATENT DOCUMENTS

| | | |
|---|---|---|
| JP | 57067858 | 4/1982 |
| JP | 7191030 | 7/1995 |
| KR | 0137420 | 2/1998 |
| WO | 88/08534 | * 11/1988 |
| WO | WO 99/41584 | 8/1999 |

OTHER PUBLICATIONS

Berry et al., Obstet. Gynecol. Jul. 1979; 54(1):43-46.*
Daniel, MD, Yair et al., "Levels of vascular endothelial growth factor are elevated in patients with ectopic pregnancy: is this a novel marker?" *Fertility and Sterility*, 72:1013-17 (1999).

(Continued)

*Primary Examiner*—Bao-Thuy L. Nguyen
(74) *Attorney, Agent, or Firm*—Heslin Rothenberg Farley & Mesiti P.C.

(57) ABSTRACT

A one-step diagnostic device for simultaneously detecting and distinguishing between a normal pregnancy and an ectopic pregnancy and methods for preparing the device are disclosed. Utilizing the device and principles of the present invention, normal pregnancy and ectopic pregnancy can be rapidly and accurately determined at an early stage by immunologically detecting the morphological differences between human chorionic gonadotropin (hCG) and modified forms thereof, which are secreted into the body fluid of a pregnant female.

6 Claims, 5 Drawing Sheets

OTHER PUBLICATIONS

Kovalevskaya, Galina et al., "Evaluation of Nicked Human Chorionic Gonadotropin Content in Clinical Specimens by a Specific Immunometric Assay," *Clinical Chemistry*, 45:68-77 (1999).

Cole, L. A., "Immunoassay of human chorionic gonadotropin, its free subunits, and metabolites," *Clinical Chemistry*, 43:2233-43 (1997).

Lapthorn, A. J. et al., "Crystal structure of human chorionic gonadotropin," *Nature*, 369:455-61 (1994).

Cole, L. A. and Kardana, A., "Discordant results in human chorionic gonadotropin assays," *Clinical Chemistry*, 38:263-70 (1992).

\* cited by examiner

DIAGNOSTIC DEVICE FOR DISTINGUISHING BETWEEN NORMAL AND ECTOPIC PREGNANCY AND METHOD FOR PREPARING THE SAME

CROSS REFERENCE TO RELATED APPLICATIONS AND CLAIM FOR FOREIGN PRIORITY BENEFITS

The present application is a continuation of International Patent Application Number PCT/KR01/01365, filed Aug. 10, 2001 and published Feb. 21, 2002 as WO 02/13685, and claims foreign priority benefits from Korean Patent Application Number 2000/46755, which was filed Aug. 12, 2000. The entire content of each of the earlier applications is incorporated herein.

FIELD OF THE INVENTION

The present invention relates to various embodiments of diagnostic devices for distinguishing between a normal pregnancy and an ectopic pregnancy and methods for preparing these devices. More particularly, the present invention relates to diagnostic devices requiring a one-step procedure for the rapid and accurate determination of a normal pregnancy versus an ectopic pregnancy at an early stage. During a normal pregnancy, human chorionic gonadotropin ("hCG") is secreted into the body fluid of the female; with an ectopic pregnancy, a modified form of hCG is secreted. The device of the present invention immunologically detects these morphological differences.

BACKGROUND ART

In a normal pregnancy, the fertilized egg implants itself within the uterine endometrial lining. With an ectopic pregnancy, the fertilized egg is implanted outside of the uterine endometrial lining. Depending upon the actual site of implantation, an ectopic pregnancy may be classified, for example, as a tubal pregnancy, a cervical pregnancy, an ovarian pregnancy, or a peritoneal pregnancy. More than 95% of ectopic pregnancies are tubal pregnancies, which therefore is often used as a general designation for an ectopic pregnancy. The etiology of ectopic pregnancy includes previous tubal ligation (contraception), PID (Pelvic Inflammatory Disease), administration of ovulation controlling formulations and STD (Sexually Transmitted Disease). The incidence of ectopic pregnancy is quite high, approaching as many as one per about 64-241 pregnant females.

Ectopic pregnancy is one of the most frequent obstetric and gynecologic emergencies, and its incidence increases year by year. Observable symptoms of tubal rupture due to an ectopic pregnancy, may include lower abdominal pain, amenorrhea, vaginal bleeding, dizziness due to a blood pressure drop, as well as, nausea and vomiting due to the gastrointestinal symptoms. Untreated tubal rupture may lead to intraperitoneal bleeding, which has emerged as the most significant cause of early stage death of pregnant females. In other words, if an ectopic pregnancy is not discovered at an early stage, tubal rupture and the associated shock from bleeding may lead to death of the patient.

Unfortunately, due to its lack of specific symptoms, and the lack of any effective method of determining the presence of an ectopic pregnancy, diagnosis of this potentially fatal condition is difficult. An efficient method of detecting ectopic pregnancy in its early stages could greatly reduce maternity-related mortality rates, and significantly reduce the anxiety associated with the uncertainty that the pregnancy is normal. Recognizing the value and importance of an efficient and effective early stage diagnostic method for determining ectopic pregnancy, the present inventors conducted extensive studies, and have successfully discovered an efficient diagnostic device for distinguishing between a normal pregnancy and an ectopic pregnancy.

hCG is produced in syncytiotrophoblast of the placenta and induces a constant production of progesterone in the early stage of pregnancy, functioning to maintain the implantation until the tenth week of pregnancy, when the placenta has become completely functional. Other know functions of hCG include, but are not limited to, the stimulation of the maternal thyroid, the stimulation of production of testosterone in the fetal testis, and plays an important role in the differentiation of internal genitalia in a male embryo. hCG is detected in the blood and urine of a pregnant female at a level of about 25 mIU/ml approximately 8 days after conception (fertilization). The concentration of hCG rises rapidly at a constant rate from the fifth week of pregnancy, whereby it reaches a concentration of about 1 IU/ml at the sixth week of pregnancy, and about 100-120 IU/ml at the tenth week of pregnancy. From this point forward, the hCG concentration decreases to reach about 20 IU/ml at the twentieth week of pregnancy, where it remains constant throughout the remainder of the pregnancy.

hCG is a glycoprotein comprised of two subunits, $\alpha$ and $\beta$, consisting of about 30% carbohydrates, and has a molecular weight of about 36,700 daltons. The $\alpha$-subunit is comprised of 92 amino acid residues, having the same structure as the $\alpha$-subunit of luteinizing hormone and thyroid stimulating hormone. The $\beta$-subunit is comprised of 145 amino acid residues (structurally characteristic of hCG) (Lapthom et al., *Nature*, 369:455-61, 1994).

Typically, hCG exists in various forms in human body fluids. Examples of forms of hCG include, for example, intact-hCG (I-hCG) and modified hCGs such as nicked hCG(N-hCG), hyperglycosylated hCG, free $\beta$-hCG and free $\beta$-core fragment. The various forms of hCG are produced during pregnancy, as well as, in the event of pituitary gland or trophoblast disease or choriocarcinoma. Intact hCG comprises about 90% of the total hCG present in a woman during a normal pregnancy, while various modified forms of hCG, such as nicked hCG and free $\beta$-hCG, comprise about 10% or less.

With an ectopic pregnancy, intact hCG comprises close to 100% of the total hCG concentration, and there are extremely small amounts of modified hCGs. In addition, the total hCG secretion, and its subsequent range of increase are significantly smaller as compared to that occurring in a female with a normal pregnancy. For example, the level of hCG secretion observed with an ectopic pregnancy is only about ⅕ of that observed with a normal pregnancy and, at the eighth week, is only about 1/50 of that seen with a normal pregnancy (i.e., about 15 IU/ml).

U.S. Pat. No. 5,786,220 discloses a process for the preparation of a one-step diagnostic reagent system that distinguishes between a normal pregnancy and an abnormal pregnancy. This reference discloses that normal pregnancy, spontaneous abortion, ectopic pregnancy, cancers, etc. can be diagnosed by simultaneously determining the concentrations of progesterone and hCG in the woman's bodily fluid. The patent teaches a method of diagnosis wherein a progesterone concentration of 25 ng/ml or lower in blood, together with an hCG concentration of about 25-2,500 mIU/ml is indicative of a spontaneous abortion or an ectopic pregnancy, and a progesterone concentration exceeding 25 ng/ml, together with an hCG concentration exceeding 2,500 mIU/ml is indicative of a normal intrauterine pregnancy.

Denil et al, *Fertility & Sterility*, 72:1013-17(1999) disclosed that the freeβ-hCG level in a normal pregnancy is typically 30-170 IU/ml; 1-70 IU/ml in an abnormal intrauterine pregnancy; and 0.059-29 IU/ml in an ectopic pregnancy, indicating that hCG degradation products are secreted to a much lower concentration in the ectopic pregnancy than in the normal pregnancy.

As discussed previously, hCG is the most important hormone in the diagnosis of pregnancy, and its level in the early stages of pregnancy, may be utilized in combination with ultrasound findings, to distinguish between a normal pregnancy, an abortion, and an ectopic pregnancy. When diagnosing pregnancy, the level of hCG in the woman's bodily fluid may be used at an early stage to confirm pregnancy. A low level of hCG, together with a rapid doubling of the hCG blood level every 1.4-2 days during the fifth to ninth weeks from conception, is typically indicative of either an abortion or an ectopic pregnancy. A greatly elevated hCG is interpreted as being indicative of multiple pregnancy or hydatidiform mole.

Ectopic pregnancy may also be diagnosed with the use of ultrasonography, diagnostic laparoscopy and the like in addition to the measurement of serum and urine hCG level in a pregnant female. Particularly, ultrasonography is conducted for diagnosis in combination with the hCG level measurement, wherein the presence of gestational sac in the ultrasound findings together with an hCG level below 1,000 mIU/ml indicates a sparse viability of the pregnancy. If the hCG level does not rise quantitatively by at least 65% per 48 hour, the prognosis of the pregnancy is determined to be very poor.

Unfortunately, the known methods of determining ectopic pregnancy, such as measuring the doubling time of the hCG level and the measuring the free β-hCG level in the body fluid of a pregnant female, are time consuming and require repeated blood sampling. The method described in the U.S. Pat. No. '220 patent is based on diagnostic principles different than those of the present invention in that the '220 method requires the contemporaneous measurement of both progesterone and hCG concentrations. Additionally, even though the distinction between a normal pregnancy and an abnormal pregnancy can be made, an effective early distinction between an ordinary spontaneous abortion and a potentially fatal ectopic pregnancy is very difficult to determine.

Accordingly, the present inventors have conducted extensive studies on the process for the preparation of a one-step simultaneous diagnosis kit by which the diagnosis of a normal pregnancy or an ectopic pregnancy can be achieved at a very early stage. As a result, the present inventors have provided a one-step diagnostic kit by which a normal pregnancy can be determined by detecting an hCG level of 25 mIU/ml, and an ectopic pregnancy can be determined through comparison between the concentrations of I-hCG and modified hCGs.

SUMMARY OF THE INVENTION

One of the many objectives of the present invention is to provide a diagnostic device for a one-step early stage diagnosis of normal pregnancy versus ectopic pregnancy, and a method for preparing the device.

The present invention utilizes an anti-I-hCG monoclonal antibody in combination with an anti-α-hCG monoclonal antibody; and an anti-modified hCG monoclonal antibody in combination with an anti-β-hCG monoclonal antibody, in order to respectively detect the I-hCG and modified hCGs present in the bodily fluids (blood, urine, saliva, etc.) of a pregnant female.

DETAILED DESCRIPTION OF THE INVENTION

Figure 1A:
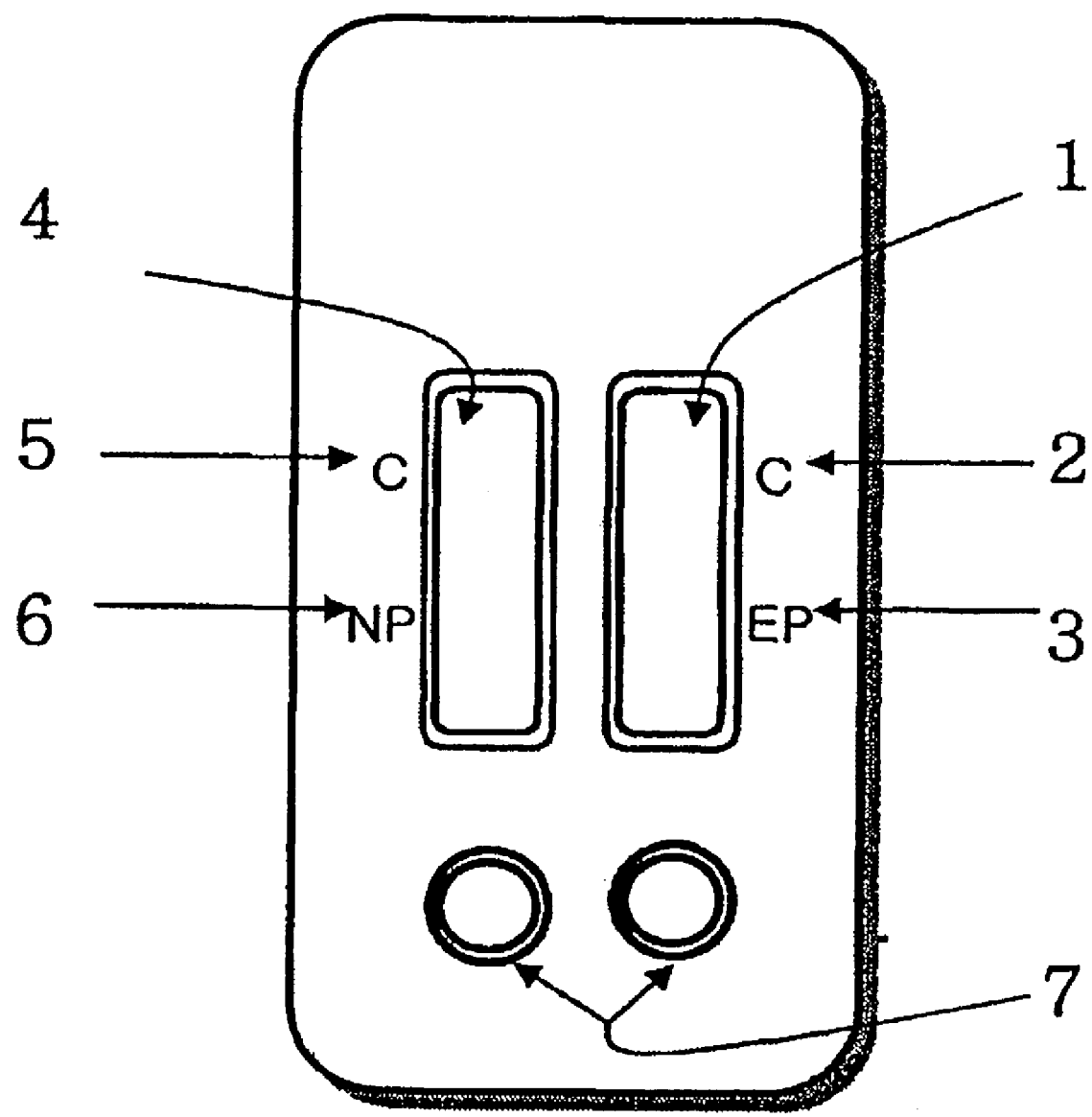
FIG. 1a shows a schematic view of a simultaneous diagnosis device for normal pregnancy and ectopic pregnancy according to the present invention. Reference numerals 1 and 4 designate reading windows of the diagnosis kit, and reference numerals 2 and 5 designate index (C) indicating the completion of the test. Reference numeral 3 designates an ectopic pregnancy line (hereinafter, referred to as "EP"), and reference numeral 6 designates a normal pregnancy line (hereinafter, referred to as "NP"). Reference numeral 7 designates a specimen receiving aperture to which a body fluid of a pregnant female is applied.

The present invention is based on an immunological assay method called a sandwich assay. In such an assay, the selection of the antibodies to be used is extremely important because the antibodies dictate the sensitivity and the specificity for the specimen to be assayed. In a sandwich assay, two kinds of monoclonal antibodies are used, wherein the binding sites for the antibodies are present on different regions of the relevant antigen in order to maintain the assay sensitivity. For example, to use a sandwich assay to examine the hCG which is secreted into body fluids (blood, urine, saliva, etc.) of a pregnant female, two kinds of monoclonal antibodies are needed and the binding sites on the antigen (hCG) for the two antibodies should be located at a distinctive distance apart. If the binding sites on the antigen (hCG) for the two antibodies are located in too close a region, steric hindrance may lead to a decrease in the assay's sensitivity.

The present invention utilizes an immuno-chromatographic method based on the sandwich assay. Particularly, a previously characterized monoclonal antibody is bound to colored fine particles (colored particulates) by covalent or non-covalent bonding, whereby the resulting particulates are used as the mobile phase. A second, previously characterized monoclonal antibody is dispensed into and immobilized onto, a nitrocellulose membrane, for use as the solid phase. The specimen to be assayed is mixed with the mobile phase and run, by capillary action, through the membrane. If a relevant antigen is contained within the specimen, the mobile phase and the solid phase are conjugated via the antigen, resulting in an observable line of the colored particulates being formed on the solid phase. Thus, the presence or absence of an observable line, visually determines the presence or absence of the relevant antigen in the specimen.

Monoclonal antibodies that may be used in the present invention are commercially available, or may be prepared according to known cell fusion protocols. The antibodies used in the present Examples were prepared according to a known process for preparing monoclonal antibody, wherein antibodies reactive to I-hCG and antibodies reactive to modified hCG were selected. For the anti-α-hCG antibody and anti-β-hCG antibody, monoclonal antibodies were selected and used, and this combination showed good sensitivity maintenance when examined using standard hCG.

As previously described, hCG is present in various forms in urine at a very early stage of pregnancy. In an ectopic pregnancy, the vast majority of hCG is present as the intact form (I-hCG), and a very little amount of modified hCG is present. To the contrary, in a normal pregnancy, I-hCG comprises only about 90% of the total hCGs present, and various modified hCGs comprise the remaining 10% or so. Relying upon the difference in hCG form concentrations, the present invention allows the confirmation of pregnancy, and at the same time, distinguishes between a normal pregnancy and an ectopic pregnancy by separately detecting and visually comparing I-hCG and modified hCGs.

The diagnostic device of the present invention comprises a device having both an ectopic pregnancy (EP) region (where a colored line appears when I-hCG is present almost exclusively in the specimen) and a normal pregnancy (NP) region (where a colored line appears when modified-hCGs are also present in the specimen). With an ectopic pregnancy, as the vast majority of the hCG is I-hCG, a colored line will appear in the EP region due to the reaction of I-hCG; it is significant to note however, that with an ectopic pregnancy, an NP line may also appear, but it will be noticeably less intense than the EP line.

With a normal pregnancy, bodily fluids contain about 10% modified hCGs in addition to the I-hCG. Accordingly, as the concentration of colored particulates having an antibody reactive to modified hCGs bound thereon is increased 2-10-fold, and the concentration of the antibody to be bound is correspondingly increased so as to enhance the reaction sensitivity with the modified hCGs, the intensity of the colored lines in the two regions (EP, NP) will be similar.

Monoclonal antibody against I-hCG, which is overexpressed in an ectopic pregnancy, is prepared according to a well-known method and then bound to colored particulates. The resulting particulates are incorporated into a glass fiber pad and dried to produce a colored particulate pad. Simultaneously, antibody against modified hCGs is also prepared according to a well-known method and then bound to colored particulates. The resulting particulates are incorporated into a glass fiber pad and dried to produce a colored particulate pad. Various colored particulates can be used in the present invention including polystyrene particles, colloidal gold, and the like. Among such particles, colloidal gold is preferable, and most preferably in a size of 20 to 60 nm.

To maintain the sensitivity of the diagnostic device, monoclonal antibodies that bind to binding sites on the antigen (hCG) which is different than the binding sites for the antibodies bound to the colored particulates were used for the solid phase membrane. The monoclonal antibodies used for this purpose are an anti-β-hCG monoclonal antibody and an anti-α-hCG monoclonal antibody. The two antibodies are immobilized on separate nitrocellulose membranes by dispensing the antibody into the membrane to respectively form a straight line (FIG. 1), or immobilized on one membrane by dispensing the antibodies into the membranes to form two crossing lines or two separate lines (FIG. 2). At an end of the membrane downstream of the monoclonal antibody-bound zone, an anti-mouse immunoglobulin polyclonal antibody is dispensed into the membrane so that a test completion line will appear.

Figure 3:
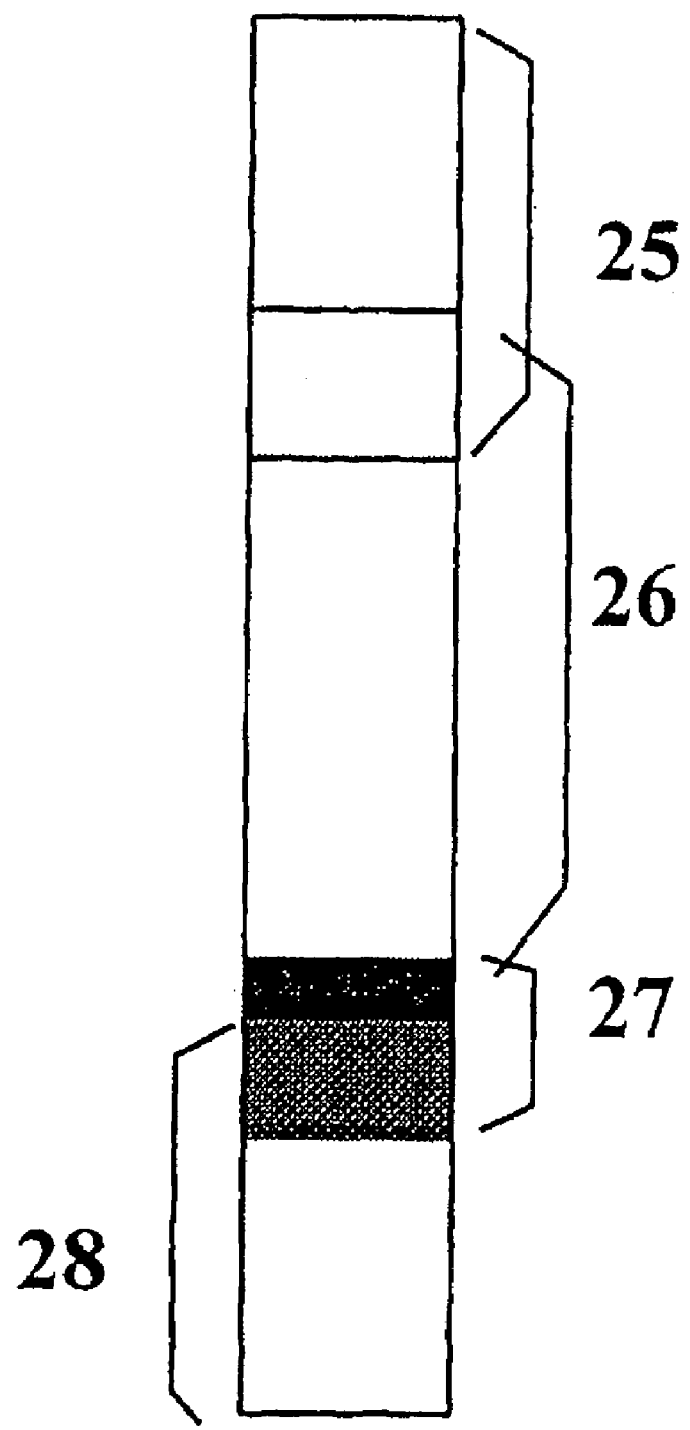
FIG. 3 shows a construction of the inner strip in the simultaneous diagnosis device for normal pregnancy and ectopic pregnancy of the present invention. Reference numeral 25 designates a specimen absorbing pad, reference numeral 26 designates an antibody-immobilized nitrocellulose membrane, reference numeral 27 designates a colored particulate pad, and reference numeral 28 designates a specimen receiving pad, wherein these pads are combined sequentially in a partially overlapping manner.

The antibody-immobilized membrane prepared as described above may be attached to a polyester support having an adhesive applied thereon, and then the monoclonal antibody-colored particulate pad is applied there over in the longitudinal direction. Subsequently, a specimen receiving pad on which the body fluid of a pregnant female is to be directly dropped, and a specimen absorbing pad for absorbing excess body fluid are applied in the longitudinal direction in a manner that the pads overlaps with each other, providing the inner strip of the simultaneous diagnosis kit for normal pregnancy and ectopic pregnancy (FIG. 3).

In practical use, for an early diagnosis of pregnancy and distinguishing between a normal and an ectopic pregnancy, a body fluid (blood, urine, saliva, etc.) specimen of a pregnant female is applied to the specimen receiving pad, the specimen is absorbed and transported by the capillary action, and then reacts with the monoclonal antibody-bound colored particulates which are incorporated in the colored particulate pad. With a normal pregnancy, I-hCG and modified hCGs present in the specimen will respectively bind to monoclonal antibodies bound on the colored particulates and move along the nitrocellulose membrane phase. In those regions where two kinds of monoclonal antibodies are immobilized on the membrane, the antigen-antibody complexes will respectively bind in a sandwich form, resulting in two result lines (NP, EP) formed by colored particulates appearing on the membrane with similar intensities.

In an ectopic pregnancy, I-hCG comprises most of the hCGs present in the body fluid, and the complex of I-hCG-bound monoclonal antibody and colored particulates will move along the membrane and bind to the anti-α-hCG monoclonal antibody to produce a strong EP band. In contrast, colored particulates having monoclonal antibody against modified hCG bound thereon will not react with I-hCG in the specimen, and consequently will move on without binding to the anti-β-hCG monoclonal antibody immobilized on the membrane. The particulates may also react with the extremely small amount of modified hCGs present in the specimen, producing a very weak NP band. Thus, if the pregnancy is ectopic, the device will show either one intense EP band, or an intense EP line and a very weak NP line.

If the tested female is not pregnant, the monoclonal antibody-colored particulate complex will move on without binding to the anti-hCG monoclonal antibody immobilized on the either the NP or the EP lines in the membrane because hCG is not present in the specimen. Consequently, the colored particulate band will appear only on the test completion line (C) where the anti-mouse immunoglobulin polyclonal antibody has been immobilized.

Examples depicting the shapes and structures of the simultaneous diagnosis device of the present invention for normal pregnancy and ectopic pregnancy are shown in FIGS. 1a to 2b.

The same results may be obtained if the antibodies bound to the colored particulate pad and the antibodies bound to the membrane are interchanged. An anti-α-hCG monoclonal antibody and an anti-β-hCG monoclonal antibody are respectively bound to colored particulates, and an anti-I-hCG monoclonal antibody, an anti-modified hCG monoclonal antibody and an anti-mouse immunoglobulin polyclonal antibody are immobilized on nitrocellulose membranes as described above to provide a diagnosis kit.

When a body fluid from a pregnant female is applied to the specimen receiving pad, one of three conditions will occur:

1) in a normal pregnancy, I-hCG and other modified hCGs present in the specimen bind to the anti-α-hCG monoclonal antibody and the anti-β-hCG monoclonal antibody respectively bound to colored particulates and move along the nitrocellulose membrane, and then respectively bind in a sandwich manner to the anti-I-hCG monoclonal antibody and the anti-modified hCG monoclonal antibody immobilized on the membrane, resulting in two result lines (NP, EP) appearing on the membrane with similar intensity;

2) in an ectopic pregnancy, I-hCG present in the body fluid binds to the anti-α-hCG monoclonal antibody bound to colored particulates and moves along the membrane, and then binds to the anti-I-hCG monoclonal antibody on the membrane, giving a strong EP band only, or the extremely small amount of modified hCG present in the specimen produces an NP band with a very weak intensity; and 3) if the tested female is not pregnant, the monoclonal antibody-colored particulate complex will move on without binding to the anti-hCG monoclonal antibody immobilized on the result lines (NP, EP) in the membrane because hCG is not present in the specimen. Consequently, the colored particulate band will appear only on the test completion line (C) where the anti-mouse immunoglobulin polyclonal antibody has been immobilized.

EXAMPLES

The present invention will now be described in more detail with reference to the following examples. It will be appreciated by a person skilled in the art that these examples are presented for illustration purposes only and are not intended to limit the scope of the present invention.

Example 1

Preparation and Purification of an Anti-I-hCG Monoclonal Antibody and an Anti-α-hCG Monoclonal Antibody A. Immunization and Cell Fusion A known cell-fusion procedure (Galfre, G. et al., *Methods Enzymol.*, 73:3-46, 1981) was used to prepare a monoclonal antibody against 1-hCG. First, 20 μg-/100 μl of 1-hCG (Zymed, USA) was fully emulsified with 100 μl of Freund's complete adjuvant and injected into a Balb/C mouse (8 weeks) intraperitoneally ("ip"). After 3 weeks, a second ip injection was conducted under the same protocol as the first injection except that 100 μl of Freund's incomplete adjuvant was used for the emulsification. After 1 week, blood samples were collected from the mouse and the antibody formation was determined by an ELISA, after which 20 μg of hCG was injected intravenously ("iv"). in the tail. Three days later, spleen cells were recovered from the mouse and cell fusion was performed using pre-cultured Sp2/O cells and PEG. The fused cells were cultured in a 96-well plate with the addition of HAT medium. Then, cells secreting antibodies reactive to I-hCG and cells secreting antibodies reactive to α-hCG were selected and subjected to large-scale culture.

B. Purification of Monoclonal Antibody

Large-scale cultures were centrifuged to remove precipitates. The supernatants were pulled and loaded onto a protein A-sepharose(FF) column, rinsed with a phosphate buffer and eluted with 0.1M glycine buffer. The eluate was dialyzed against a phosphate buffer to adjust the concentration and used for the preparation of diagnosis kits.

Example 2

Preparation and Purification of an Anti-Modified hCG Monoclonal Antibody and an Anti-β-hCG Monoclonal Antibody Spleen cells were obtained from a mouse which had been immunized three times with a β-hCG antigen purchased from Zymed according to the same procedure as in Example 1, A. The cells were admixed with Sp2/O cells and cell fusion was conducted using PEG. The fused cells were cultured in a 96-well plate with the addition of HAT medium. Then, cells secreting antibodies reactive to β-hCG and cells secreting antibodies reactive to modified hCGs without reactivity to intact hCG were selected and subjected to large-scale culture. Subsequently, monoclonal antibodies were purified from large-scale cultures according to the same purification procedures as in Example 1, B, adjusted the concentration after dialyzing against a phosphate buffer, and then used for the preparation of diagnosis kits.

Example 3

Preparation of Colloidal Gold (Colored Particulates)

Colloidal gold of 20-60 nm in size was used as colored particulates. To prepare the colloidal gold, 220 ml of double distilled water was put into a 500 ml round-bottomed flask. The flask was then placed over a hot plate (Coming, USA) and a reflux apparatus (Pyrex, USA) was equipped to prevent the evaporation of water. The hot plate was turned on to heat the flask to 100° C. with suspension. When the temperature of the distilled water exceeds 100° C., 1.0 ml of 2% gold chloride (Sigma, USA) was added with intimate mixing followed by 2.0 ml of 1% sodium citrate (Sigma, USA). Heating was continued for further 30 minutes to produce colloidal gold. The colloidal gold thus produced was filtered on a 0.45 µm filter paper to remove impurities and aggregates, and then used for the preparation of diagnostic device.

Example 4

Preparation of Colored Particulate Pads in Which Colored Particulates Having a Monoclonal Antibody Bound Thereto are Incorporated To prepare colored particulates having a monoclonal antibody bound thereto, 50 ml aliquots of the colored particulates prepared in Example 3 were placed individually in beakers. Monoclonal antibodies prepared in Examples 1 and 2 were respectively added into the flasks in an amount of 1-15 µg per 1 ml of colored particulates with stirring, and reacted for 2 to 30 min. After completion of the reaction, a blocking solution containing 1-10% bovine serum albumin was added into each beaker to a final albumin concentration of 0.1-1% and reacted for 2 to 30 min.

The reaction mixture was put into 50 ml centrifuge tubes (Corning, USA) and centrifuged in an ultracentrifuge (Backman, USA) at 10,000 rpm for 15 min. After centrifuge, the supernatants were discarded, and the precipitates were removed and resuspended in a stabilizing buffer (0.5-2% bovine serum albumin, 1-5% sucrose, 50-100 mM Tris™ HCl buffer (pH 7.5-9.0)). The resulting suspensions were adjusted for an adequate concentration, and colored particulate pads were soaked in the suspensions and then dried. Colored particulates having the anti-modified hCG monoclonal antibody obtained in Example 2 bound thereto were added to a concentration as high as 2 to 10 times the concentration of colored particulates having the anti-I-hCG monoclonal antibody obtained in Example 1 bound thereto. Alternatively, a 2 to 10 fold higher concentration of the anti-modified hCG monoclonal antibody was used for the binding reaction, such that modified hCGs, which are contained in the test specimen in a relatively small amount (10%), can be clearly detected.

When the anti-β-hCG monoclonal antibody obtained in Example 2 and the anti-α-hCG monoclonal antibody obtained in Example 1 were formulated into colored particulate pads, the concentration of the anti-modified hCG monoclonal antibody which was bound to the membrane was adjusted to be 2 to 10 times higher than the concentration of the anti-I-hCG monoclonal antibody so that modified hCGs can be clearly detected.

Example 5

Preparation of Antibody-Immobilized Membranes (Readout Panel)

To make result lines reacting in response to normal pregnancy and ectopic pregnancy within zones where an antibody is immobilized, monoclonal antibody recognizing and binding α-hCG and monoclonal antibody recognizing and binding µ-hCG were dropped onto a nitrocellulose membrane to respectively form straight lines. The antibodies were prepared at a concentration of 1 to 4.0 mg/ml and dropped and immobilized on the membrane to a final concentration of 0.1 µg to 5 µg/cm, where a 5-50 mM phosphate buffer containing 0.1 to 2% sucrose was used as the immobilization solution. Downstream to the monoclonal antibody-dropped zone, reaction completion line (C in FIGS. 1a and 2b) was provided using a rabbit anti-mouse immunoglobulin (IgG) polyclonal antibody at a concentration of 0.5-2 mg/ml, wherein a 5-50 mM phosphate buffer containing 0.1 to 2% sucrose was used as the immobilization solution. Membranes where the antibody immobilization had been completed were dried at room temperature for 2 hours. The antibody to be immobilized and the drop pattern can be varied according to the shape of the result lines to be displayed.

Figure 1B:
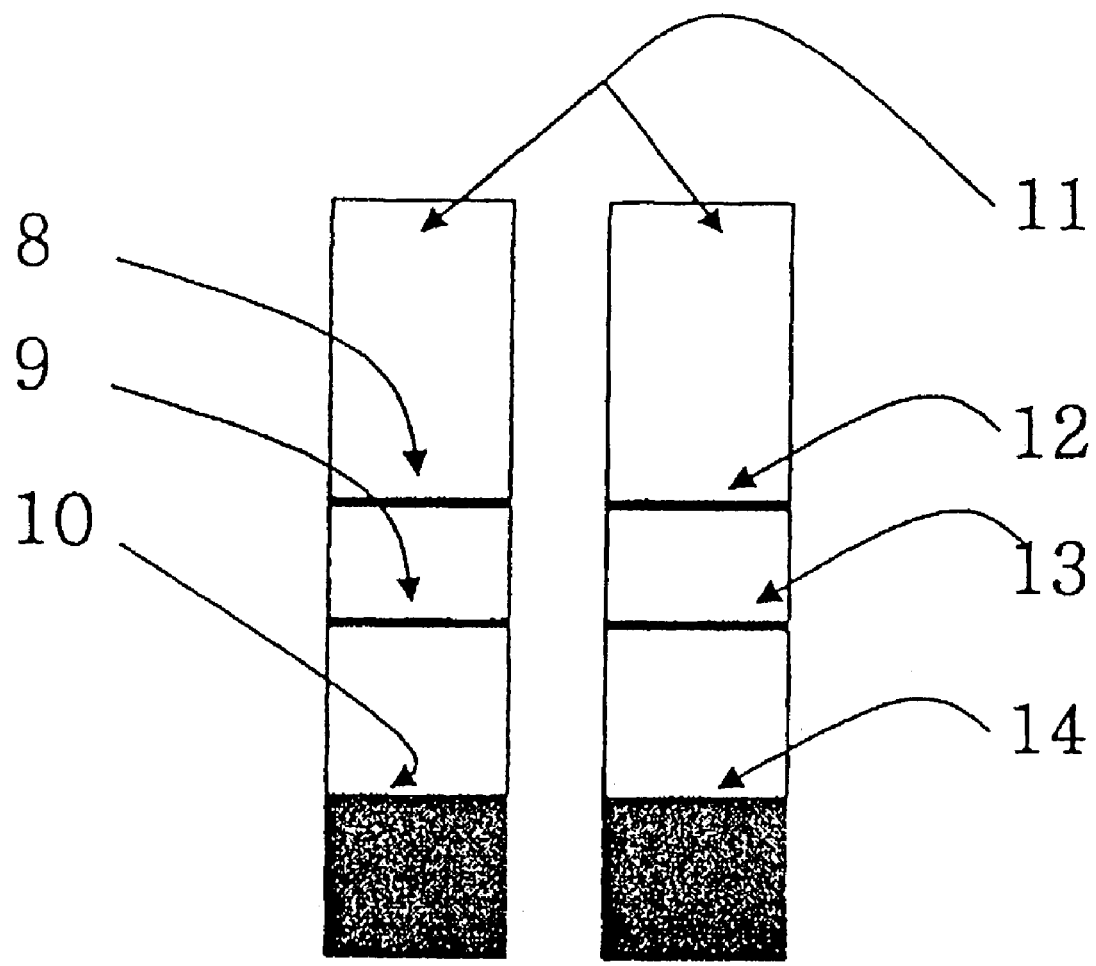
FIG. 1b schematically shows the result lines (NP, EP) and the completion line (C) on the antibody-immobilized membrane used for the inner strip in FIG. 1a. Reference numeral 11 designates a nitrocellulose membrane. Reference numerals 8 and 12 designate completion lines where a rabbit anti-mouse immunoglobulin polyclonal antibody has been immobilized. Reference numeral 9 designates a test result line where an anti-β-hCG monoclonal antibody has been immobilized, and reference numeral 13 designates a test result line where an anti-α-hCG monoclonal antibody has been immobilized. Reference numeral 10 designates a pad of colored particulates having an anti-modified hCG monoclonal antibody bound thereon, and reference numeral 14 designates a pad of colored particulates having an anti-I-hCG monoclonal antibody bound thereon.
Figure 2A:
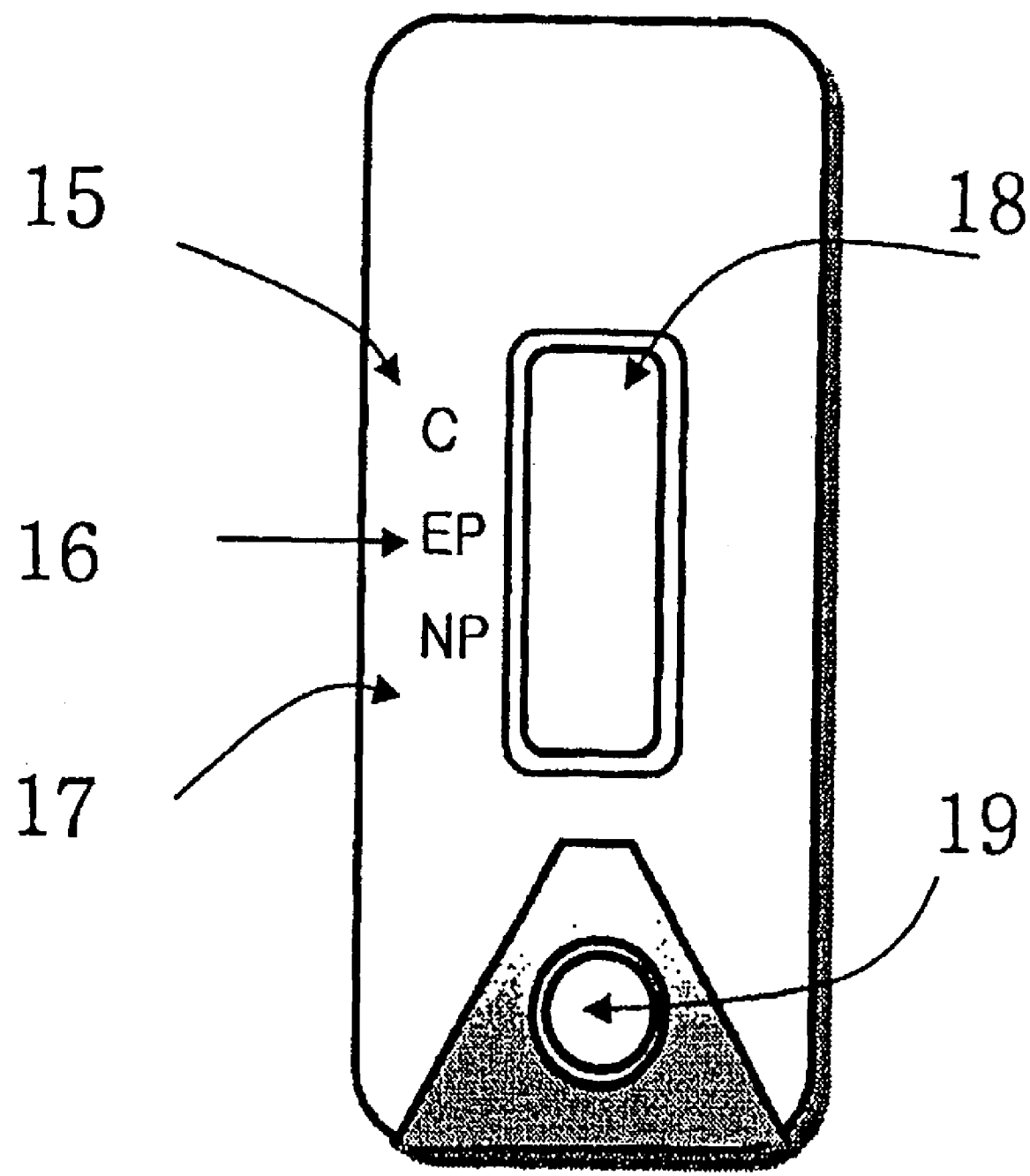
FIG. 2a shows another schematic view of a simultaneous diagnosis device for normal pregnancy and ectopic pregnancy according to the present invention. Reference numeral 15 designates an index (C) indicating the completion of the test. Reference numeral 16 designates an ectopic pregnancy line (EP) and reference numeral 14 designates a normal pregnancy line (NP). Reference numeral 18 designates a reading window of the diagnostic device, and reference numeral 19 designates a specimen receiving aperture to which a body fluid specimen of a pregnant female is applied.
Figure 2B:
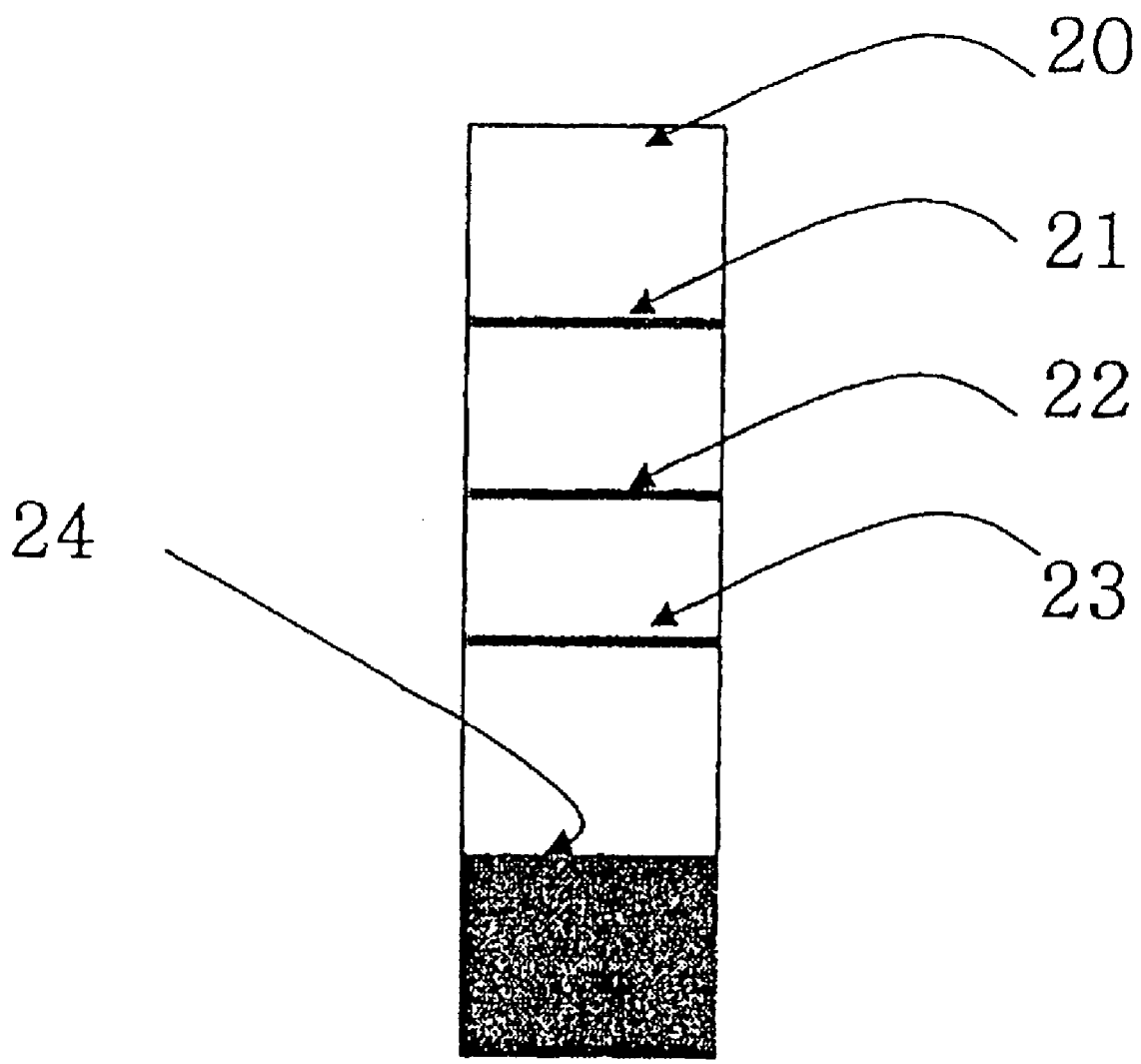
FIG. 2b schematically shows the result lines (NP, EP) and the completion line (C) on the antibody-immobilized membrane used for the inner strip in FIG. 2a. Reference numeral 20 designates a nitrocellulose membrane. Reference numeral 21 designates a completion line where a rabbit anti-mouse immunoglobulin polyclonal antibody has been immobilized. Reference numeral 22 designates an ectopic pregnancy (EP) line where an anti-α-hCG monoclonal antibody has been immobilized, and reference numeral 23 designates a normal pregnancy (NP) line where an anti-β-hCG monoclonal antibody has been immobilized. Reference numeral 24 designates a pad of mixed colored particulates having an anti-modified hCG monoclonal antibody and an anti-I-hCG monoclonal antibody bound thereon.

The diagnostic kit shown in FIG. 1 was prepared by dropping and immobilizing an anti-α-hCG monoclonal antibody and an anti-p-hCG monoclonal antibody on different membranes. In the diagnosis kit shown in FIG. 2, the two antibodies were dropped and immobilized on one membrane in the form of two straight lines spaced apart in order to make the result lines appear on one membrane. Particularly for a diagnosis kit as shown in FIG. 1, the selection of the antibody to be immobilized on the membrane and the antibody to be bound to the colored particulates is very important for obtaining the desired results. Thus, when a membrane having an anti-α-hCG monoclonal antibody immobilized thereon is used, a colored particulate pad having an anti-I-hCG monoclonal antibody bound thereto is desirably used. When a membrane having an anti-β-hCG monoclonal antibody immobilized thereon is used, a colored particulate pad having an anti-modified hCG monoclonal antibody bound thereto is desirably used so that modified hCG can be detected. When a membrane having an anti-modified hCG monoclonal antibody immobilized thereon is used, a colored particulate pad having an anti-β-hCG monoclonal antibody bound thereto is used. If a membrane having an anti-I-hCG monoclonal antibody immobilized thereon is used, a colored particulate pad having an anti-α-hCG monoclonal antibody bound thereto is desirably used.

Example 6

Specimen Receiving Pad and Specimen Absorbing Pad

Glass fiber (Millipore, USA) or cellulose paper (Whatman, England) was used in the specimen receiving pad and cellulose paper (Whatman, England) was used in the specimen absorbing pad.

Example 7

Preparation of a Strip for Simultaneous Diagnosis of Pregnancy and Ectopic Pregnancy As depicted in FIG. 3, the antibody-immobilized membrane prepared in Example 5 was attached to an adhesive polyester support, and the antibody-bound colored particulate pad prepared in Example 4 was applied there over with an overlap of 1-3 mm. The specimen receiving pad was then applied with an overlap of 1-10 mm in the longitudinal direction followed by the specimen absorbing pad with an overlap of 1-5 mm to give a simultaneous diagnosis strip. The resulting simultaneous diagnosis strip was assembled into a plastic housing such as those shown in FIGS. 1a and 2a to produce a simultaneous diagnostic kit for normal pregnancy and ectopic pregnancy.

Experimental Example 1

Evaluation of the Simultaneous Diagnosis Kit Using an hCG Standard Solution

To evaluate the specificity of the diagnosis kit prepared according to the above Examples, an hCG standard solution was prepared from I-hCG commercially available from Zymed (Cat. No. 14-1401) and the urine of a pregnant female at her early stage of pregnancy who had been determined to have a normal pregnancy on the basis of ultrasound findings. Colored particulate pads for the kit to be evaluated were prepared by binding a monoclonal antibody against I-hCG and a monoclonal antibody against modified hCGs respectively to colored particulates as in Example 4. Antibody bound membranes were prepared by dropping an anti-α-hCG monoclonal antibody and an anti-β-hCG monoclonal antibody respectively on nitrocellulose membranes as in Example 5. The resulting two kinds of antibody-fixed membranes and two kinds of colored particulate pads were assembled to provide every possible combination of membrane and pad. Then, specimen receiving pads and specimen absorbing pads were respectively attached to the assemblies to produce simultaneous diagnostic strips.

As standard solutions, negative and positive standards were prepared and used in the tests.

Negative standard 50 mM phosphate buffer (pH 7.2)

Positive standard 1 I-hCG 50 mIU/ml phosphate buffer (pH 7.2)

Positive standard 2 Urine from a female of an early stage pregnancy wherein ultrasound findings confirmed the normal intrauterine gestational sac and the heart beat of the fetus had been detected.

The above standard solutions were applied to the specimen receiving zones at an amount of about 500 μl and observed for 3 minutes. The appearance or absence of a result line indicated "positive" and "negative" for the result. The test results are listed in Table 1 below.

TABLE 1

Comparison of recognition properties for the monoclonal antibodies used for the simultaneous diagnosis kits (1)

| Standard | Antibody bound on membrane | Antibody bound to colored particulates | |
|---|---|---|---|
| | | anti-modified hCG monoclonal antibody | anti-I-hCG monoclonal antibody |
| Negative standard | anti-β-hCG antibody | − | − |
| | anti-α-hCG antibody | − | − |
| Positive standard 1 | anti-β-hCG antibody | + | + |
| | anti-α-hCG antibody | + | ++ |

TABLE 1-continued

Comparison of recognition properties for the monoclonal antibodies used for the simultaneous diagnosis kits (1)

| Standard | Antibody bound on membrane | Antibody bound to colored particulates | |
|---|---|---|---|
| | | anti-modified hCG monoclonal antibody | anti-I-hCG monoclonal antibody |
| Positive standard 2 | anti-β-hCG antibody | +++ | + |
| | anti-α-hCG antibody | + | +++ |

Notes:
− (no reaction)
+ (very little reaction)
++ (significant reaction)
+++ (strong reaction)

As can be seen from Table 1, in the case of the negative standard which does not contain hCG, the result is determined to be "negative" because there appear no lines within those zones on the membrane where antibody 1 and 2 are immobilized. For the positive standard 1 containing I-hCG, colored particulates having an anti-I-hCG monoclonal antibody bound thereto and the zone where an anti-α-hCG monoclonal antibody is immobilized showed a strong interaction and kits with other monoclonal antibodies showed weak interactions. For the positive standard 2 utilizing urine from a female with a normal pregnancy, colored particulates having an anti-I-hCG monoclonal antibody bound thereto and the zone where an anti-α-hCG monoclonal antibody is immobilized showed a strong interaction. Colored particulates having an anti-modified hCG monoclonal antibody bound thereto and the zone where an anti-β-hCG monoclonal antibody is immobilized also showed a strong interaction. From these results, it could be recognized that an anti-I-hCG monoclonal antibody in combination with an anti-α-hCG monoclonal antibody can detect I-hCG, while the detection of modified hCGs can be achieved by using an anti-modified hCG monoclonal antibody and an anti-β-hCG monoclonal antibody.

Similar results were obtained when the antibodies bound to colored particulates and the membrane were interchanged, clearly indicating the importance of the combination of the antibodies used in the assay. Table 2 shows the results from a test with a standard hCG solution, wherein an anti-α-hCG monoclonal antibody and an anti-β-hCG monoclonal antibody are bound to colored particulates and an anti-I-hCG monoclonal antibody and an anti-modified hCG monoclonal antibody were immobilized on the membrane to prepare a simultaneous diagnostic kit.

TABLE 2

Comparison of recognition properties for the monoclonal antibodies used for the simultaneous diagnosis kits (2)

| | | Antibody bound to colored particulates | |
|---|---|---|---|
| Standard | Antibody bound on membrane | anti-β-hCG monoclonal antibody | anti-α-hCG monoclonal antibody |
| Negative standard | anti-modified hCG antibody | − | − |
| | anti-I-hCG antibody | − | − |
| Positive standard 1 | anti-modified hCG antibody | + | + |
| | anti-I-hCG antibody | + | ++ |

TABLE 2-continued

Comparison of recognition properties for the monoclonal antibodies used for the simultaneous diagnosis kits (2)

| | | Antibody bound to colored particulates | |
|---|---|---|---|
| Standard | Antibody bound on membrane | anti-β-hCG monoclonal antibody | anti-α-hCG monoclonal antibody |
| Positive standard 2 | anti-modified hCG antibody | +++ | + |
| | anti-I-hCG antibody | + | +++ |

(-) no reaction
(+) very little reaction
(++) significant reaction
(+++) strong reaction As seen in the above experimental example, normal pregnancy and ectopic pregnancy could be determined with naked eyes because the location and intensity of the appearing lines varied depending on the form of the hCG contained in the specimen.

Experimental Example 2

Assay on the Urine of a Pregnant Female Using a Kit for the Simultaneous Diagnosis of Normal Pregnancy and Ectopic Pregnancy Table 3 shows the results from a test where urine samples obtained from a non-pregnant female, a female with normal pregnancy, and a female with ectopic pregnancy were applied respectively to simultaneous diagnosis kits of the present invention for assaying modified-hCGs and I-hCG which are specifically found in normal pregnancy and ectopic pregnancy. The urine sample for normal pregnancy was obtained from a pregnant female for whom ultrasound finings confirmed intrauterine gestational sac and the heart beat of the fetus had been detected. The urine sample for ectopic pregnancy was obtained from a female for whom the ectopic pregnancy findings were confirmed through a surgical operation. The diagnosis kits used in this example were in the form shown in FIG. 1a.

As is seen from Table 3, no lines appeared at the result lines for NP and EP in the case of the urine sample from a non-pregnant female. In the case of the urine sample from a female with normal pregnancy, the result lines for NP and EP appeared with similar intensity. In particular, for the urine sample from a female with ectopic pregnancy, a much stronger line appeared at the result line for EP than that for NP, which means that the readout allows a sharp distinction between normal pregnancy and ectopic pregnancy.

INDUSTRIAL APPLICABILITY

The present invention provides one-step pregnancy diagnosis devices that can simultaneously detect normal pregnancy and ectopic pregnancy and methods for the preparation of such devices. Since the body fluid of a pregnant female contains different forms of hCG depending on the form of the pregnancy, the present invention allows a rapid and accurate detection of normal pregnancy and ectopic pregnancy at an early pregnancy stage, by immunologically detecting the forms of hCG present in the body fluid. In the present invention, an anti-I-hCG monoclonal antibody is combined with an anti-α-hCG monoclonal antibody and an anti-modified hCG monoclonal antibody is combined with an anti-β-hCG monoclonal antibody in order to individually detect I-hCG and modified hCGs present in the body fluid of a pregnant female. Consequently, the present invention will be useful in reducing the maternity mortality by finding ectopic pregnancy at an early stage.

We claim:
1. A pregnancy diagnosis device comprising:
a) a specimen receiving pad;
b) particulate pad comprising colored particulates bound to anti-α-hCG and anti-β-hCG monoclonal antibodies for detecting hCGs in a specimen;
c) a membrane having a plurality of indicator lines including:
  (i) an ectopic pregnancy indicator line defined by the presence of an anti-I-hCG monoclonal antibody;
  (ii) a normal pregnancy indicator line defined by presence of an anti-modified hCG monoclonal antibody; and

TABLE 3

Determination of clinical accuracy of the simultaneous diagnostic kit

| | | Specimen Number | | | | | | | | | |
|---|---|---|---|---|---|---|---|---|---|---|---|
| Type of Specimen | Line | 1 | 2 | 3 | 4 | 5 | 6 | 7 | 8 | 9 | 10 |
| Urine non-pregnant | NP | − | − | − | − | − | − | − | − | − | − |
| | EP | − | − | − | − | − | − | − | − | − | − |
| Urine normal pregnancy | NP | +++ | +++ | +++ | +++ | +++ | +++ | +++ | +++ | +++ | +++ |
| | EP | +++ | +++ | +++ | +++ | ++ | +++ | +++ | ++ | +++ | +++ |
| Urine ectopic pregnancy | NP | + | − | + | + | − | − | + | − | − | + |
| | EP | +++ | +++ | +++ | +++ | +++ | +++ | +++ | +++ | +++ | +++ |

(−) no reaction
(+) very little reaction
(+++) strong reaction (iii) a test completion indicator line defined by presence of an anti-mouse immunoglobulin polyclonal antibody, wherein an indicator line becomes visible when analyte bound to colored particulates is captured by a cognate antibody and wherein an ectopic pregnancy is indicated by a stronger ectopic pregnancy indicator line relative to the normal pregnancy indicator line.

2. The pregnancy diagnosis device according to claim 1, wherein the anti-α-hCG monoclonal antibody and the anti-β-hCG monoclonal antibody has been dissolved in an immobilization buffer containing 0.1%-2% sucrose and 5-50 mM phosphate buffer and then immobilized onto the membrane to 0.1-5 μg/cm.

3. The pregnancy diagnosis device according to claim 1, wherein the specimen is selected from urine, blood and saliva.

4. The pregnancy diagnosis device of claim 1, wherein anti-α-hCG and anti-IhCG monoclonal antibodies are interchangeable.

5. The pregnancy diagnosis device of claim 1, wherein anti-β-hCG and anti-modified hCG monoclonal antibodies are interchangeable.

6. The device of claim 1, wherein when a specimen from a non-pregnant female is tested, only the test completion line is visually observable;

when a specimen from a female with a normal pregnancy is tested, the test completion line, the ectopic pregnancy line and the normal pregnancy line are visually observable with equal intensities; and when a specimen from a female with an ectopic pregnancy is tested, only the test completion line and the ectopic pregnancy line are visually observable, or alternatively the test completion line, the ectopic pregnancy line, and the normal pregnancy line are turned visually observable with the intensity of the normal pregnancy line being weaker than the test completion and ectopic pregnancy lines.

* * * * *

UNITED STATES PATENT AND TRADEMARK OFFICE
CERTIFICATE OF CORRECTION

| | |
|---|---|
| PATENT NO. | : 7,332,350 B2 |
| APPLICATION NO. | : 10/364715 |
| DATED | : February 19, 2008 |
| INVENTOR(S) | : Chang et al. |

It is certified that error appears in the above-identified patent and that said Letters Patent is hereby corrected as shown below:

Claim 4, Col. 15, Line 19: Delete "anti-IhCG" and insert -- anti-I-hCG --

Signed and Sealed this

Seventeenth Day of June, 2008

JON W. DUDAS
*Director of the United States Patent and Trademark Office*